United States Patent
Chen

(10) Patent No.: US 11,045,662 B2
(45) Date of Patent: Jun. 29, 2021

(54) WEARABLE EYEBROW-IRRADIATING DEVICE

(71) Applicant: Chung-Yang Chen, Xindian (TW)

(72) Inventor: Chung-Yang Chen, Xindian (TW)

(*) Notice: Subject to any disclaimer, the term of this patent is extended or adjusted under 35 U.S.C. 154(b) by 134 days.

(21) Appl. No.: 16/152,028

(22) Filed: Oct. 4, 2018

(65) Prior Publication Data

US 2020/0108269 A1 Apr. 9, 2020

(51) Int. Cl.
*A61N 5/00* (2006.01)
*A61N 5/06* (2006.01)

(52) U.S. Cl.
CPC .... *A61N 5/0617* (2013.01); *A61N 2005/0647* (2013.01)

(58) Field of Classification Search
CPC .................................. A61N 5/00; A61N 5/06
USPC ...................................................... 607/88, 91
See application file for complete search history.

(56) References Cited

U.S. PATENT DOCUMENTS

| | | | | |
|---|---|---|---|---|
| 5,503,637 A * | 4/1996 | Kyricos | ................ | A61M 21/00 600/27 |
| 10,272,259 B1 * | 4/2019 | Blanche | ............... | A61N 5/0617 |
| 2003/0181961 A1 * | 9/2003 | Kamei | .................. | A61M 21/00 607/88 |
| 2008/0262575 A1 * | 10/2008 | Aunio | ................... | A61M 21/00 607/88 |
| 2009/0307828 A1 * | 12/2009 | Ludlow | .................. | A61F 9/029 2/431 |
| 2013/0041432 A1 * | 2/2013 | Tucker | ................. | A61N 5/0617 607/89 |
| 2015/0374971 A1 * | 12/2015 | Dar | .................... | A61N 1/36014 607/139 |

\* cited by examiner

*Primary Examiner* — Jennifer Pitrak McDonald
*Assistant Examiner* — Sana Sahand
(74) *Attorney, Agent, or Firm* — Muncy, Geissler, Olds & Lowe, P.C.

(57) ABSTRACT

A wearable eyebrow-irradiating device includes a main irradiation body, a circumferential light-shielding lining and a fastening headband. The main irradiation body, worn on user's head, has at least one lighting component for projecting respective eyebrow-growth stimulating beams onto corresponding eyebrow-growing zones upon when the main irradiation body is fitted onto the head. The circumferential light-shielding lining, mounted fixedly at the main irradiation body by surrounding the lighting component, is to shield the eyebrow-growing zone, so that an eye can be isolated from the neighboring eyebrow-growing zone. The fastening headband, connecting the main irradiation body, is to wear the main irradiation body tightly onto the head, and to elastically deform the circumferential light-shielding lining so as to completely shield the eyebrow-growing zone and thus to prevent the eyebrow-growth stimulating beam from irradiating the eye.

5 Claims, 6 Drawing Sheets

US 11,045,662 B2

WEARABLE EYEBROW-IRRADIATING DEVICE

BACKGROUND OF THE INVENTION

1. Field of the Invention

The invention relates to a wearable eyebrow-irradiating device, and more particularly to the wearable eyebrow-irradiating device that incorporates a circumferential light-shielding lining and a fastening headband to shield an eyebrow-growing zone so as not to leak optical beams for stimulating and growing an eyebrow.

2. Description of the Prior Art

Currently, in the art, some manufacturers have developed various portable eyebrow-irradiating devices for growing eyebrows. However, the portable device is mainly mounted to ears of respective user in a hanging manner like wearing glasses, or directly clamped to user's head, such that an irradiation section of the portable device can target an eyebrow-growing zone on the head. Also, no matter whether the portable device is a hanging eyebrow-irradiating device or a clamping eyebrow-irradiating device, an foreseeable situation is that the device can't fit firmly on each of many different heads. In addition, the irradiation section is usually furnished with a light source mounted inside a hole so as to confine a projection angle and a projection range of the light source. Thus, in practice, when a user wears one of the aforesaid eyebrow-irradiating devices, it is quite possible that the eyebrow-irradiating device would be dislocated or misaligned by unexpected shakes or collisions results from ill fit between the device and user's head. More seriously, the irradiation section might slip down to a place that the irradiating beams could jeopardize user's eyes.

SUMMARY OF THE INVENTION

In view of the aforesaid ill-fit concern upon any of the conventional eyebrow-irradiating devices, thus when the eyebrow-irradiating device is impacted to dislocate, the irradiation section would be quite possible to harm user's eyes through direct irradiation, and further to cause serious body risk. Accordingly, it is an object of the present invention to provide a wearable eyebrow-irradiating device that can increase wearing stability of the device on user's head so as further to prevent the lighting component from irradiating user's eyes.

In the present invention, the wearable eyebrow-irradiating device includes a main irradiation body, a circumferential light-shielding lining and a fastening headband.

The main irradiation body, applied to be worn on a head of a user, has at least one lighting component for projecting at least one eyebrow-growth stimulating beam onto at least one eyebrow-growing zone on the head upon when the main irradiation body is fitted onto the head. The circumferential light-shielding lining, mounted fixedly at the main irradiation body by surrounding the at least one lighting component, is to shield the at least one eyebrow-growing zone upon when the main irradiation body is fitted onto the head, so that an eye close to the at least one eyebrow-growing zone is isolated from the at least one eyebrow-growing zone. The fastening headband, connecting the main irradiation body, is to wear the main irradiation body tightly onto the head, and to elastically deform the circumferential light-shielding lining so as to completely shield the at least one eyebrow-growing zone and thus to prevent the at least one eyebrow-growth stimulating beam from irradiating the eye.

In one embodiment of the present invention, the circumferential light-shielding lining further has an extension portion for contacting a root of nose upon when the main irradiation body is fitted to the head.

In one embodiment of the present invention, the circumferential light-shielding lining is made of a silicone.

In one embodiment of the present invention, the fastening headband is detachably connected with the main irradiation body.

In one embodiment of the present invention, the fastening headband includes a first fixation structure, a second fixation structure and a belt body, the first fixation structure and the second fixation structure being detachably connected with the main irradiation body, two opposing ends of the belt body being engaged with the first fixation structure and the second fixation structure, respectively. Preferably, the belt body is made of a silicone, and the belt body is an elastic band.

As stated above, since the wearable eyebrow-irradiating device provided by the present invention is consisted of the main irradiation body, the circumferential light-shielding lining and the fastening headband, thus the main irradiation body can be fitted tightly onto user's head by the fastening headband, and the circumferential light-shielding lining can be elastically deformed to completely shield the at least one eyebrow-growing zone and thus to prevent the eye from being irradiated by the at least one eyebrow-growth stimulating beam. Upon such an arrangement, wearing stability of the eyebrow-irradiating device can be effectively improved, and also possible optical leakage of the eyebrow-growth stimulating beams can be substantially avoided.

All these objects are achieved by the wearable eyebrow-irradiating device described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

The invention disclosed herein is directed to a wearable eyebrow-irradiating device. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
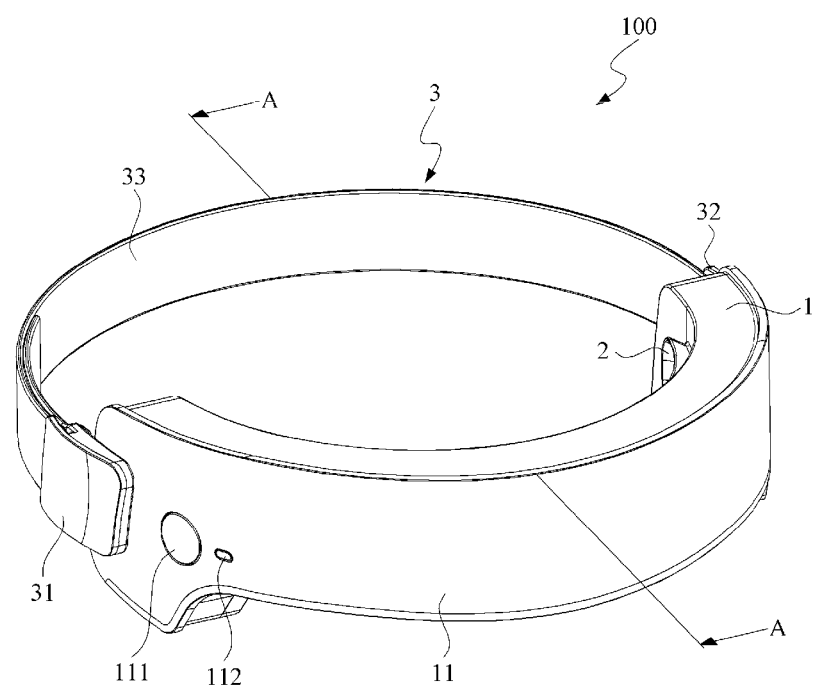
FIG. 1 is a schematic perspective view of a preferred embodiment of the wearable eyebrow-irradiating device in accordance with the present invention.
Figure 2:
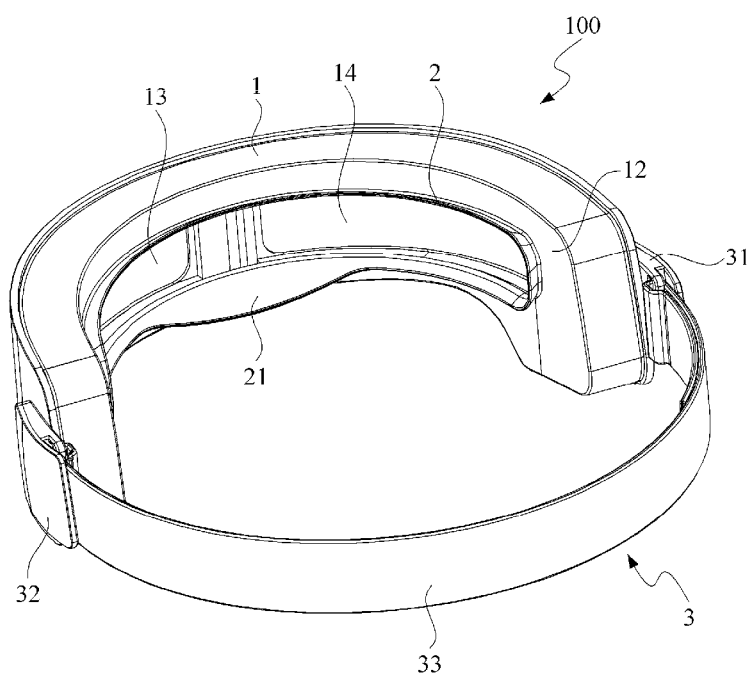
FIG. 2 demonstrates schematically another view of FIG. 1.

Refer now to FIG. 1 and FIG. 2; where FIG. 1 is a schematic perspective view of a preferred embodiment of the wearable eyebrow-irradiating device in accordance with the present invention, and FIG. 2 demonstrates schematically another view of FIG. 1.

As shown, the wearable eyebrow-irradiating device 100 includes a main irradiation body 1, a circumferential light-shielding lining 2 and a fastening headband 3.

The main irradiation body 1 has an outer surface 11, an inner surface 12 and two lighting components 13 and 14. The outer surface 11 is furnished with a start button 111 and an indicator 112. The start button 111 is used for activating the main irradiation body 1, and the indicator 112 is to show an operation state of the main irradiation body 1. The inner surface 12 is located oppositely to the outer surface 11, with respect to the main irradiation body 1. The two lighting components 13 and 14, both embedded on the inner surface 12, are used to generate at least one eyebrow-growth stimulating beam (not shown in the figure). In the present invention, each of the lighting components 13 and 14 can be a semiconductor laser or an LED, and the eyebrow-growth stimulating beam can be a visible red light having a wavelength range within 620-1000 nm or a near-infrared.

The circumferential light-shielding lining 2 is installed fixedly on the inner surface 12 of the main irradiation body 1 by surrounding the lighting components 13 and 14. In this embodiment, the circumferential light-shielding lining 2 can be made of silicone, rubber, foam, or the like opaque material.

The fastening headband 3 includes a first fixation structure 31, a second fixation structure 32 and a belt body 33. The first fixation structure 31 and the second fixation structure 32 are individually and detachably fixed to opposing portions of the outer surface 11, and two opposing ends of the belt body 33 are engaged with the first fixation structure 31 and the second fixation structure 32, respectively. Thereupon, the entire fastening headband 3 can be connected with the main irradiation body 1 in a detachable manner. In this embodiment, the belt body 33 can be an elastic band including a silicone portion.

Figure 3:
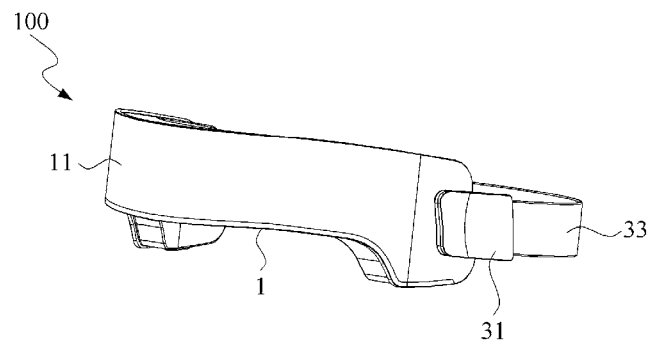
FIG. 3 is a schematic perspective view showing separately and user and the preferred embodiment of the wearable eyebrow-irradiating device in accordance with the present invention.
Figure 3:
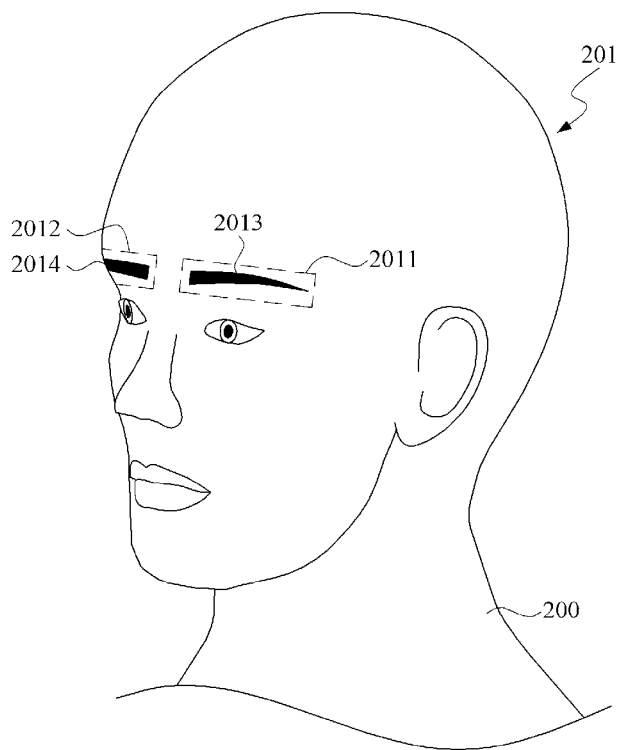
Figure 4:
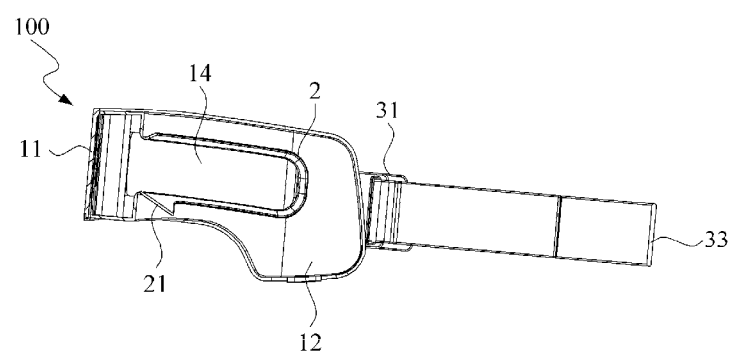
FIG. 4 demonstrates schematically another view of FIG. 3, specifically with the wearable eyebrow-irradiating device in a cross-sectional view along line A-A of FIG. 1.
Figure 4:
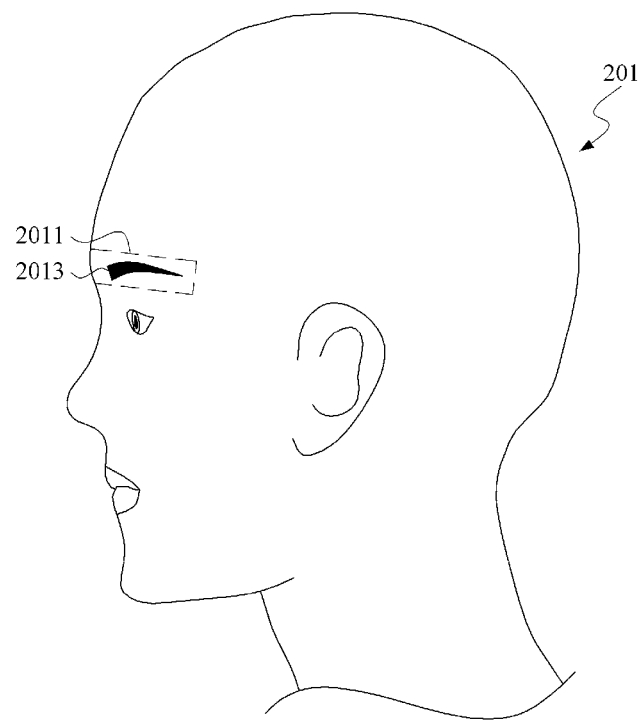

Refer now to FIG. 3 and FIG. 4; wherein FIG. 3 is a schematic perspective view showing separately and user and the preferred embodiment of the wearable eyebrow-irradiating device in accordance with the present invention, and FIG. 4 demonstrates schematically another view of FIG. 3, specifically with the wearable eyebrow-irradiating device in a cross-sectional view along line A-A of FIG. 1.

As shown, the wearable eyebrow-irradiating device 100 of the present invention is to be worn on a head 201 of a user 200, in which the head 201 of the user 200 has two eyebrow-growing zones 2011 and 2012, growing an eyebrow 2013 and another eyebrow 2014, respectively.

While the main irradiation body 1 is positioned to the head 201, the two lighting components 13 and 14 are to projects respective eyebrow-growth stimulating beams onto the corresponding eyebrow-growing zones 2011 and 2012. At this time, the circumferential light-shielding lining 2 shields both the eyebrow-growing zones 2011 and 2012. In this embodiment, since the red light or the near-infrared is introduced to irradiate the eyebrow-growing zones 2011 and 2012, thus growth of the eyebrows 2013 and 2014 in the respective eyebrow-growing zones 2011 and 2012 can be effectively promoted.

Figure 5:
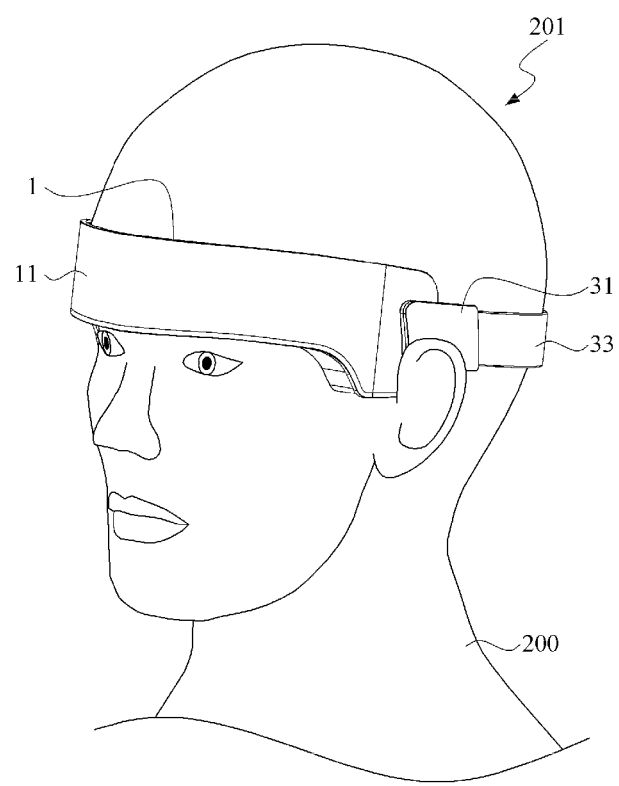
FIG. 5 is a schematic perspective view of the wearable eyebrow-irradiating device worn on a head of user in accordance with the present invention.
Figure 6:
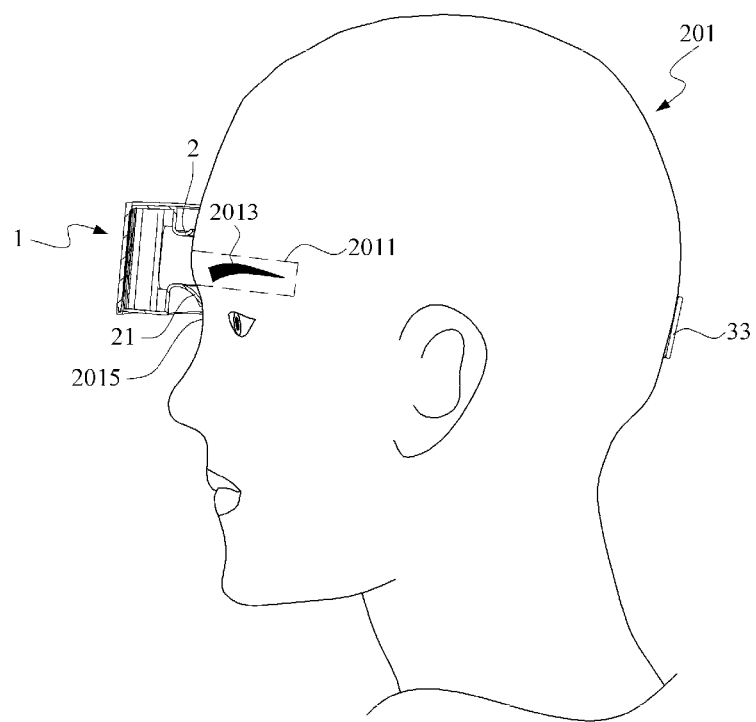
FIG. 6 demonstrates schematically another view of FIG. 5, specifically with the wearable eyebrow-irradiating device in a cross-sectional view along line A-A of FIG. 1.

Refer now to FIG. 5 and FIG. 6; wherein FIG. 5 is a schematic perspective view of the wearable eyebrow-irradiating device worn on a head of user in accordance with the present invention, and FIG. 6 demonstrates schematically another view of FIG. 5, specifically with the wearable eyebrow-irradiating device in a cross-sectional view along line A-A of FIG. 1.

As shown, the main irradiation body 1 is tightly fitted onto the head 201 of the user 200 via the application of the belt body 33. Preferably, while in the tight fit, the circumferential light-shielding lining 2 is deformed elastically so as to have the main irradiation body 1 positioned firmly on the head 201 and to entirely shield both the eyebrow-growing zones 2011 and 2012. Thereupon, when the two lighting components 13 and 14 project respective eyebrow-growth stimulating beams onto the corresponding eyebrow-growing zones 2011 and 2012, no optical leakage is possible. In addition, with the help of the circumferential light-shielding lining 2 in positioning and shielding, the risk of the eyebrow-growth stimulating beam hitting eyes of the user would be completely removed.

In addition, the circumferential light-shielding lining 2 further provides an extension portion 21 to contact a root of nose 2015 upon when the main irradiation body 1 is fitted to the head 201. Thereby, the circumferential light-shielding lining 2 can be still fitted to the head 201, even that the contour protrusion exists at the root of nose 2015.

In summary, in comparison to the conventional hanging or clamping eyebrow-irradiating device that is barely fitted to user's head, so that the risk of hurting user's eyes due to a false position of the irradiation section caused by unexpected impacts does always exist, the wearable eyebrow-irradiating device provided by the present invention can fit the main irradiation body tightly onto user's head by introducing the fastening headband and the circumferential light-shielding lining, and thus can further shield the eyebrow-growing zones completely. Upon such an arrangement, wearing stability of the eyebrow-irradiating device can be effectively improved, and also possible optical leakage of the eyebrow-growth stimulating beams can be substantially avoided.

While the present invention has been particularly shown and described with reference to a preferred embodiment, it will be understood by those skilled in the art that various changes in form and detail may be without departing from the spirit and scope of the present invention.

What is claimed is:

1. A wearable eyebrow-irradiating device, to be worn on a head of a user having two eyebrow-growing zones, comprising:
    a main irradiation body, configured to be positioned on the head of the user, having an outer surface, an inner surface and two lighting components embedded on the inner surface for projecting at least one eyebrow-growth stimulating beam onto at least one of the two eyebrow-growing zones when the main irradiation body is fitted onto the head;
    a fastening headband, connected with the main irradiation body in a detachable manner for the main irradiation body to be worn tightly onto the head; and
    one circumferential light-shielding lining, mounted fixedly on the inner surface to surround both of the two lighting components, made of one of silicone, rubber and foam, further having an extension portion;

wherein, when the main irradiation body is tightly fitted onto the head via the fastening headband, the one circumferential light-shielding lining is deformed elastically onto the head with the extension portion contacting a root of nose of the user so as to have the main irradiation body to be positioned firmly on the head and thus to entirely shield light emitted from the two lighting components to only emit the light on the two eyebrow-growing zones, so that an eye close to any of the two eyebrow-growing zones is isolated from any of the two eyebrow-growing zones.

2. The wearable eyebrow-irradiating device of claim 1, wherein the fastening headband includes a first fixation structure, a second fixation structure and a belt body, the first fixation structure and the second fixation structure being detachably connected with the main irradiation body, two opposing ends of the belt body being engaged with the first fixation structure and the second fixation structure, respectively.

3. The wearable eyebrow-irradiating device of claim 2, wherein the belt body is made of a silicone.

4. The wearable eyebrow-irradiating device of claim 2, wherein the belt body is an elastic band.

5. The wearable eyebrow-irradiating device of claim 1, wherein the outer surface is furnished thereon with a start button for activating the main irradiation body and an indicator for showing an operation state of the main irradiation body.

\* \* \* \* \*